United States Patent [19]

Foley

[11] Patent Number: 5,059,741
[45] Date of Patent: Oct. 22, 1991

[54] C5/C6 ISOMERIZATION PROCESS
[75] Inventor: Richard M. Foley, Houston, Tex.
[73] Assignee: Shell Oil Company, Houston, Tex.
[21] Appl. No.: 647,078
[22] Filed: Jan. 29, 1991
[51] Int. Cl.$^5$ ................................................. C07C 5/13
[52] U.S. Cl. ................................... 585/734; 585/750; 585/751
[58] Field of Search ..................... 585/734, 750, 751

[56] References Cited
U.S. PATENT DOCUMENTS

| | | | |
|---|---|---|---|
| 4,176,053 | 11/1979 | Holcombe | 208/310 |
| 4,210,771 | 7/1980 | Holcombe | 585/701 |
| 4,717,784 | 1/1988 | Stem et al. | 585/738 |
| 4,804,802 | 2/1989 | Evans et al. | 585/734 |
| 4,855,529 | 8/1989 | Stem et al. | 585/737 |

Primary Examiner—Curtis R. Davis
Attorney, Agent, or Firm—Y. Grace Tsang

[57] ABSTRACT

An integrated process for the production of a refinery gasoline pool with enhanced octane value from a pentane and hexane containing feedstock by first contacting with an isomerization catalyst; fractionating the resulting product into an iC$_5$ product stream forming part of said refinery gasoline pool and a bottom stream containing nC$_5$, nC$_6$, mono-branched C$_6$ and dibranched C$_6$; passing said bottom stream through an adsorption bed with dibranched C$_6$ passing thru unabsorbed; desorbing nC$_5$, nC$_6$ and monobranched C$_6$ from the absorption bed; and recycling the desorbed nC$_5$, nC$_6$ and monobranched C$_6$ to the isomerization zone.

20 Claims, 1 Drawing Sheet

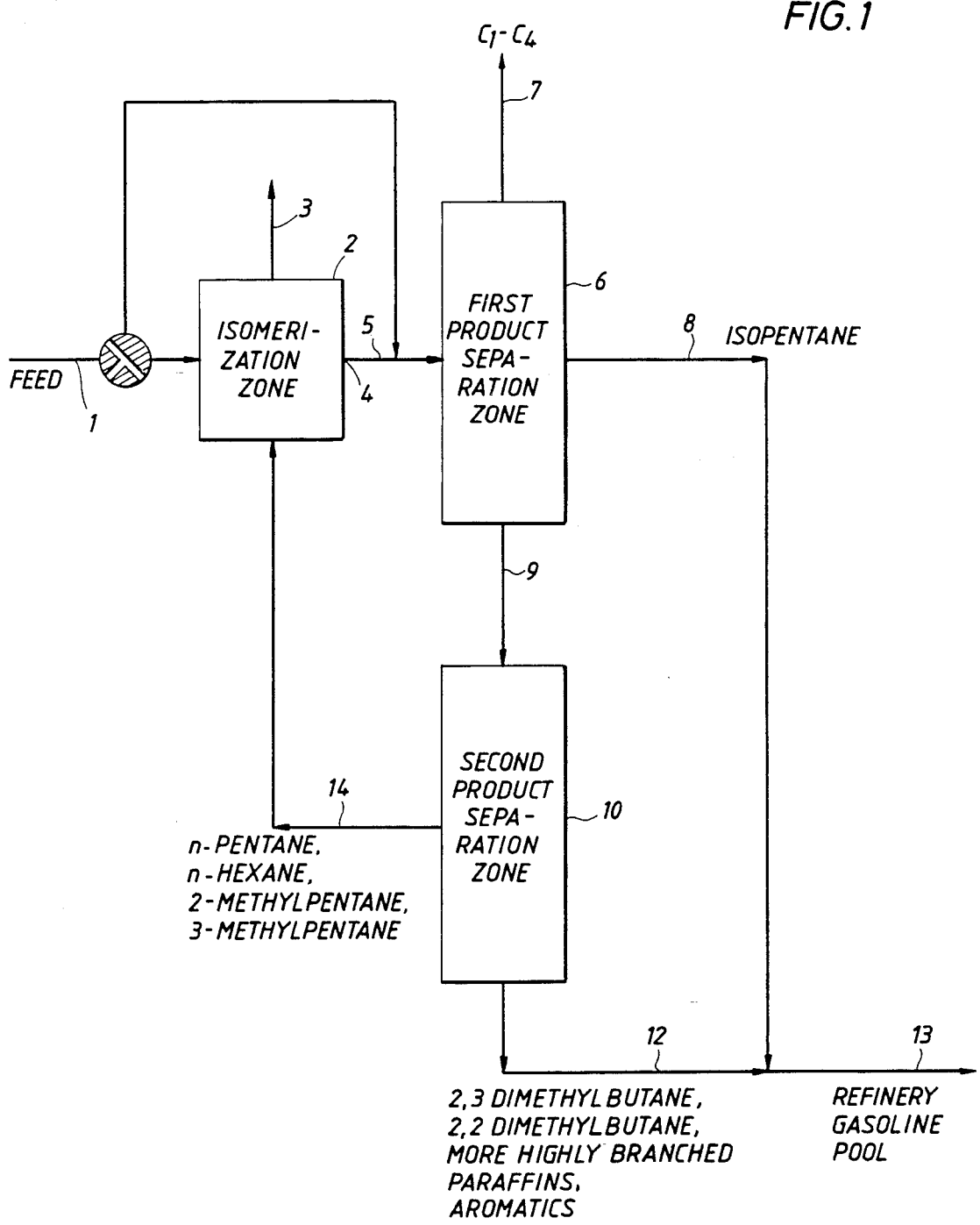

C5/C6 ISOMERIZATION PROCESS

FIELD OF THE INVENTION

This invention relates to a process for increasing the octane number of an isomerate gasoline blending component by increasing the amount of di-methyl-branched paraffins and isopentane in the isomerate and reducing the quantity of mono-methyl-branched hexanes.

BACKGROUND OF THE INVENTION

As a result of pollution and environmental problems, retail gasolines in the United States will eventually have a phased down lead content. Maintenance of high octane gasolines by methods other than lead addition is of continuing interest to U.S. refiners. Three major techniques are available to acquire high octane gasoline pools without lead addition. First, hydrocarbons can be reformed in the presence of a reforming catalyst, such as a platinum-rhenium catalyst, to a high octane gasoline. Second, alcohol-based oxygenates, such as methyl tertiary butyl ether (MTBE) can be added to motor gasoline to obtain enhanced octane ratings. Third, normal paraffins can be isomerized to branched paraffins possessing high octane qualities. The present invention concerns the third process and is an improvement over prior art isomerization process.

In Holcombe, U.S. Pat. No. 4,210,771, a basic process referred to as a Total Isomerization Process (TIP) is disclosed in which a feedstream consisting essentially of mixed normal and branched hydrocarbons is passed first through an isomerization reactor and the products therefrom passed to an adsorption section which separates normal from branched paraffins to form an isomerate having di- and mono-branched paraffins and a recycle stream of nearly pure normal paraffins. The resultant gasoline therefore contains mono-branched hexanes which have an inherently lower octane rating than the di-branched paraffins and the mono-branched pentane.

A second Holcombe patent, U.S. Pat. No. 4,176,053, discusses a normal paraffin-isomerization separation process. A molecular sieve is employed to separate normal paraffins from a feedstock mixture comprising normal and branched paraffins, and only normal paraffins are adsorbed and fed to the isomerization reactor after void space purging of the molecular sieve absorbent.

U.S. Pat. No. 4,717,784, issued to Evans et al on Jan. 5, 1988, discloses a process for the isomerization of feed streams comprising $C_6$ or $C_6{}^+$ normal paraffins with recycle of mono-methyl-branched paraffins and normal paraffins. A separation zone downstream of the isomerization reactor is comprised of a sieve having a pore size between $5.5 \times 5.5$ Å and $4.5 \times 4.5$ Å which permits the adsorption of mono-methyl-branched paraffins and normal paraffins while allowing the dimethyl paraffins to pass through the sieve and be collected as the isomerate product stream. Both normal olefins and all the mono-branched olefins are absorbed in the separation zone and recycled to the isomerization zone. If the feed stream contains pentanes, this process would result in the recycling of high-octane-rated mono-branched pentane and would therefore result in a build up of mono-branched pentane in the process. Thus, the feedstocks claimed in the process taught by Evans are limited to $C_6$ or greater carbon atoms. Since most commercial feedstocks contain pentanes, the process is therefore not commercially viable.

A second Evans patent, U.S. Pat. No. 4,804,802, issued on Feb. 14, 1989, is an improvement on the separation technique used in the isomerization process taught in the above-mentioned Evans, U.S. Pat. No. 4,717,784. The separation zone downstream of the isomerization reactor is comprised of a first separatory sieve having a pore size smaller than or equal to $4.5 \times 4.5$ Å to adsorb normal paraffins while allowing mono-methyl-branched paraffins and di-branched paraffins to pass through the sieve. The second sieve is a molecular sieve having a pore size greater than $5.5 \times 5.5$ Å and less than $4.5 \times 4.5$ Å which will adsorb the mono-methyl-branched paraffins while allowing the dimethyl paraffins to pass through the sieve and be collected as the isomerate product stream. The feedstocks claimed in the process are again limited to $C_6$ or greater carbon atoms. As discussed above, if the feed stream contains pentanes, this process would also result in the recycling of high-octane-rated mono-branched pentane and would therefore result in a build up of mono-branched pentane in the process which would likewise not be commercially viable.

A third Evans patent, U.S. Pat. No. 4,855,529, issued on Aug. 8, 1989, is an improvement process upon the isomerization process taught in the above-mentioned Evans, U.S. Pat. No. 4,804,802. The process is similar to that taught in the U.S. Pat. No. 4,855,529 except that the di-branched paraffins in the feedstocks are separated prior to the isomerization step. The process is likewise not commercially feasible for the isomerization of pentane containing feedstocks.

The feedstream to a Total Isomerization Process is usually derived from refinery operations and normally is comprised mainly of isomeric forms of saturated hydrocarbons having five and six carbon atoms. After isomerization, the product stream is comprised primarily of n-pentane, isopentane (mono-branched $C_5$), n-hexane, dimethylbutanes (di-branched hexanes), and methylpentanes (mono-branched hexanes). As illustrated in the TABLE 1 below, di-branched hexanes and mono-branched pentane (isopentane) have high octane numbers. However, mono-branched hexanes (methylpentanes) have relatively low octane numbers. It is, therefore, advantageous to develop a process which would recycle the low-octane-rated methylpentanes and normal paraffins, but recover, without recycling, the high-octane-rated isopentane and di-branched hexanes.

TABLE 1

The ASTM $C_5$ and $C_6$ Octane Numbers

| Component | ASTM Research Octane Numbers (0.0 mL TEL/gal) |
|---|---|
| n-Pentane | 62 |
| 2-Methylbutane (isopentane) | 93 |
| n-Hexane | 25 |
| 2-Methylpentane | 73 |
| 3-Methylpentane | 75 |
| 2,2-Dimethylbutane | 92 |
| 2,3-Dimethylbutane | 104 |

In the Total Isomerization Process (TIP) taught by Holcombe, di-branched hexanes are recovered along with all the mono-branched paraffins and only normal paraffins are recycled to the isomerization zone. The resultant gasoline contains mono-branched hexane which has an inherently low octane rating as indicated in the TABLE 1 above.

In the prior art processes disclosed by Stem et al, both normal paraffins and all the mono-branched paraffins are absorbed in a molecular sieve type separation zone and recycled to the isomerization zone. If the feed stream contains pentanes, this process would result in the recycling of high-octane-rated mono-branched pentane and would therefore result in a build up of mono-branched pentane in the process. Since most commercial feedstocks contain pentanes, this process is therefore not commercially viable.

Accordingly, there remains a demand for an integrated isomerization process that is commercially viable for converting a $C_5$ and $C_6$ containing feedstocks to an isomerate gasoline blending component with higher octane number and which process would recover both the di-methyl-branched paraffins and mono-methyl-branched pentane (i.e. isopentane) in the isomerate, but recycle the low octane rated mono-methyl-branched hexanes (i.e. methylpentanes) and normal paraffins. The instant invention provides such a process.

SUMMARY OF THE INVENTION

The present invention is related to an integrated process for the production of a refinery gasoline pool with enhanced octane value from a pentane and hexane containing feedstock by first contacting said feedstock with an isomerization catalyst; fractionating the resulting product into an $iC_5$ product stream forming part of said refining gasoline pool and a bottom stream containing $nC_5$, $nC_6$, mono-branched $C_6$ and dibranched $C_6$; passing said bottom stream through an adsorption zone comprising a bed containing a molecular sieve having a pore size between $5.5 \times 5.5$ Å and $4.5 \times 4.5$ Å and causing dibranched $C_6$ to pass through unadsorbed, forming part of said refining gasoline pool; deadsorbing $nC_5$, $nC_6$ and monobranched $C_6$ from the adsorption bed and recycling said desorbed $nC_5$, $nC_6$ and monobranched $C_6$ to the isomerization reactor.

OBJECTS OF THE INVENTION

An object of this invention is to provide an integrated isomerization/adsorption process wherein both normal paraffins and mono-methyl-branched hexanes are recycled to the isomerization zone.

Another object of this invention is to provide a total isomerization product with a maximum content of di-methyl branched paraffins, such as 2,3-dimethylbutane, and mono-methyl-branched pentane (2-methyl butane).

Another object of this invention is to provide an isomerization process able to attain a product stream of higher octane value than previously recognized.

Yet another object of this invention is to provide an integrated process wherein normal pentane and normal hexane are converted to an isomerate product having an increased quantity of isopentane and 2,3-dimethylbutane, and a decreased quantity of methylpentanes.

BRIEF DESCRIPTION OF THE DRAWINGS

FIG. 1 is a schematic flow scheme of the novel process of this invention utilizing a first separation zone to recover isopentane. Normal paraffins and isohexanes are adsorbed and recycled.

DETAILED DESCRIPTION OF THE INVENTION

The instant invention involves an integrated process for the production of a refinery gasoline pool with enhanced octane value from a pentane and hexane containing feedstock by contacting with an isomerization catalyst; fractionating the resulting product into an $iC_5$ product stream and a bottom stream containing $nC_5$, $nC_6$, mono-branched $C_6$ and dibranched $C_6$; passing said bottom stream through an adsorption bed with dibranched $C_6$ passing thru unadsorbed; desorbing $nC_5$, $nC_6$ and monobranched $C_6$ from the absorption bed; and recycling the desorbed $nC_5$, $nC_6$ and monobranched $C_6$ to the isomerization catalyst.

The schematic process flow of this invention exemplified by FIG. 1 is initiated by the introduction of a hydrocarbon feedstock 1 either to an isomerization zone 1 or to a first product separation zone 2.

Isomerization Step

In a preferred embodiment of the present invention, the feedstock 1 is introduced to the isomerization zone 2 having an isomerization catalyst therein. Contemplated feed streams to this embodiment of the present process are comprised mainly of isomeric forms of saturated hydrocarbons having $C_5$ and $C_6$ or greater carbon atoms. The feed stream can comprise normal paraffins, mono-methyl paraffins and dimethyl paraffins. The carbon numbers of these paraffins are preferably $C_5$ or higher for the normal paraffins, mono-methyl-branched paraffins and di-branched paraffins. These feedstocks are usually derived from refinery operations and can contain quantities of $C_4-$, $C_7+$, and cyclic paraffins. Small quantities of olefinic and aromatic hydrocarbons may also be present. As a non-limiting illustrative example, a feedstream comprising a fresh feed having 1.05 wt % $C_1$ to $C_4$; 30.31 wt % n-$C_5$ paraffins, 30.80 wt % iso-$C_5$, 11.47 wt % n-$C_6$, 14.37 wt % 2-methyl pentane, 5.69 wt % 3-methyl pentane, 2.43 wt % 2,3-dimethyl butane, 1.77 wt % 2,2-dimethyl butane, small quantities of cycloparaffins, aromatics, and $C_7$ paraffin can be utilized.

Suitable isomerization catalysts which can be used in the isomerization zone 2 include any catalyst known to one skilled in the art which would isomerize normal paraffins to branched paraffins and which would crack parraffins with more than six carbon atoms into $C_6$ or smaller chain paraffins. Some suitable catalysts are described in Column 5 of U.S. Pat. No. 4,210,771, all of the teachings of which is herein incorporated by reference. Typically, the catalyst comprises a catalytic metal selected from Group VIII of the Periodic Table of Elements. Preferably, the catalytic metal is a noble Group VIII metal such as platinum, palladium, osmium, ruthenium, iridium and/or rhodium, etc.

Optionally, the catalytic metal can be deposited on an alumina base which has been activated by the addition of chlorine. The catalytic metal can also be deposited on zeolite molecular sieves. Suitable zeolite molecular sieves include zeolites which have a silica to alumina molar ratio of greater than 3 and less than 60 and, preferably, less than 15 and may have many monovalent and polyvalent metal cations exchanged with the sieve, such as those of the alkali metals or alkaline earth metals. The isomerization catalyst can be present per se or it may be mixed with a binder material. Typical binder materials are inorganic oxide diluent materials such as oxides of the metals of Group VI of the Mendeleev Periodic Table of the Elements, e.g. chromium, molybdenum and tungsten; aluminas, silicas, the oxides of metals of Groups III, IV-A and IV-B of the Medndeleev Periodic Table, and cogels of silica and oxides of the metals of the Groups III, IV-A and IV-B, especially alumina, zirconia, titania, thoria and combinations thereof. Aluminosilicate clays such as kaolin, attapulgite, sepiolite, polygarskite, bentonite, montmorillonite and the like when rendered in a pliant plastic-like condition by intimate admixture with water are also suitable diluent materials, particularly when said clays have not been acid-washed to remove substantial quantities of alumina. A non-limiting example of such a catalyst includes mordenite with platinum present in a range of 0.005 wt % to 10.0 wt % with a preferred range being from 0.2 to 0.4 wt %. Another example is a platinum or palladium metal in an amount of about 0.1 to 1.0 weight percent deposited on a zeolitic material prepared from zeolite Y having a $SiO_2/Al_2O_3$ molar ratio of about 5 by reducing the sodium cation content to less than about 15 equivalent percent by ammonium cation exchange, then introducing between about 35 and 50 equivalent percent of rare earth metal cations by ion exchange and thereafter calcining the zeolite to effectuate substantial deammination.

The isomerization conditions present in the isomerization zone 2 are those selected to maximize the conversion of normal paraffins and mono-methyl-paraffins to di-methyl-branched paraffins. This type of isomerization is favored in the vapor phase with a fixed bed of isomerization catalyst. If desirable, a vented hydrogen or light hydrocarbon gas stream can be removed from the isomerization zone in conduit 3. Typical operating temperatures include from about 200° to about 400° C. with pressures of about 10 to 40 bar. Even at these select conditions, the effluent from the isomerization reactor will still contain substantial (e.g. 20 to 30 wt %) normal paraffins and mono-methyl-branched paraffins which are unreacted or partially reacted.

The isomerization effluent stream 4 typically is comprised of paraffins with high octane values such as $C_5$ mono-branched pentane (isopentane) and $C_6$ di-branched paraffins (i.e. 2,2-dimethylbutane and 2,3-dimethylbutane); and low octane valued paraffins such as $C_5$ normal paraffin, $C_6$ normal paraffin, $C_6$ mono-branched paraffins (i.e. 2-methylpentane and 3-methylpentane), and $C_1$–$C_4$ light ends. Paraffins with more than six carbon atoms are cracked into $C_6$ or smaller chain paraffins.

First Product Separation Step

The isomerization zone effluent stream 4 is sent to a first product separation zone 6 which is designed to separate high octane rated $C_5$ mono-branched paraffins (isopentane) from $C_5$ normal paraffin, $C_6$ normal paraffin, $C_6$ mono-branched paraffins and $C_6$ di-branched paraffins. As an illustrative, but non-limiting example, the first product separation zone 6 can be a distillation column (i.e., fractional distillation column). Mono-methyl-branched pentane (isopentane) has a very low boiling point, 27.8° C. at 1 atmospheric pressure, and is lower than that of normal $C_5$ paraffin, and that of all the isomerates of $C_6$ paraffins, the fractionation step can therefore be designed to recover mono-methyl-branched pentane (isopentane) as the top stream and a stream comprising $C_5$ normal paraffin, $C_6$ normal paraffin, $C_6$ mono-branched paraffins and $C_6$ di-branched paraffins as the bottom stream. Light ends 7 which are sometimes generated during isomerization can also be removed by the fractionation distillation step. The $C_5$ mono-branched paraffins (isopentane) 8 recovered ar combined with the effluent 11 from the second product separation zone which effluent typically is comprised of dimethylbutane and, occasionally when present, small quantities of cycloparaffins to form the isomerate product gasoline blending component of the present invention.

Second Product Separation Step

The bottom stream 9 from the first product separation zone 6, e.g. the distillation column, is passed to a second product separation zone 10, which can comprise a single absorbent bed or can comprise from about 2 to about 20 absorbent beds and will be operated in an adsorption/desorption mode as exemplified in U.S. Pat. No. 4,210,771, all of the teachings of which, in regard to the function of adsorption/desorption are herein incorporated by reference. Each absorbent bed may contain a single shape-selective molecular sieve or may contain multiple sections each contain shape-selective sieves having pore sizes of different dimensions.

As the first configuration for the second product separation zone of the present invention, a single shape-selective molecular sieve is utilized. The molecular sieve must be one effective to separate mono-methyl-branched paraffins and normal paraffins from more highly branched paraffins (e.g. di-branched paraffins). As an illustrative example, a molecular sieve having precise pore dimensions between the channel pore dimensions present in either a calcium-5A sieve or a ZSM-5 sieve can be utilized. The particular molecular sieve of this category is capable of adsorbing not only normal hexane but also mono-branched hexanes (methylpentanes) as well. The preferred molecular sieve has eight and ten member rings and pore dimensions between $5.5 \times 5.5$ and $4.5 \times 4.5$ Å, but excluding $4.5 \times 4.5$ Å (i.e., calcium 5A) Angstroms. As a preferred aspect of this configuration, ferrierite, either the natural form or the synthetic form, is utilized as the molecular sieve in a single shape-selective sieve containing separation zone. This aluminosilicate exhibits a greatly increased adsorption capacity towards methylpentane relative to a calcium-5A molecular sieve. It has been discovered that both the sodium and the hydrogen forms of the ferrierite are viable although it is preferred that the ferrierite be utilized with a cation of an alkali metal, or alkaline earth metal or transition metal Other examples of the suitable molecular sieves of this type include aluminophosphates, silicoaluminophosphates, and borosilicates. Exemplary of the wide range of aluminophosphates available in the prior art are the following articles:

1) Synthesis And Properties Of Several Aluminophosphate Molecular Sieves; Quinhua, Xu; Dong, Jialu; Yan, Aizhen; Jin, Changtai Dep. Chem., Nanjing Univ., Nanjing, Peopl. Rep. China, Acta. Phys. Chem., 31(1–2), 99–108 66-3 (Surface Chemistry and Colloids)

2) Synthesis Of Aluminophosphate Molecular Sieve, AlPO4–12, Xu, Wen Yang; Guo, Chang Jie; Do. Tao Shanxi, Peopl. Rep. China J. Inclusion Pheno., 4(4), 325–31 66-63 (Surface Chemistry and Colloids)

3) Synthesis And Properties Of New Aluminophosphate Molecular Sieves, CNU−n (n=1,2,3) Xu, Qinhua; Dong, Jialu; Yan, Aizhen; Jin, Changtai Dep. Chem., Nanjing Univ. Nanjing, Peopl. Rep. China Wuji Huaxue, 1, 74–80

4) Structural Features Of Aluminophosphate Materials With Aluminum/Phophorus-1, Bennett, J. M.; Dytrych, W. J.; Pluth, J. J.; Richardson, J. W., Jr.; Smith, J. V. Inorganic Chemicals and Reactions 78-5, Union Carbide Corp. Tarrytown, N.Y. 10591, USA 5) Zeolites, (5), 349–60 75-0 (Crystallography and Liquid Crystals) The Structure Of Coprecipitated Aluminophosphate Catalyst Supports, Cheung, T. T. P.; Willcox, K. W.; McDaniel, M. P.; Richardson, Johnson, M. M.; Bronnimann, C.; Frye, J. Phillips, Res. Cebt, Bartlesville, Okla. 74004, USA, J. Catal., 102(1), 10–20 67-1 (Catalysis, Reaction Kinetics, and Inorganic Reaction Mechanisms)

6) Site Energy Distribution And Catalytic Properties of Microporous Crystalline A1PO4-5, Choudhary, Vasant R.; Akolekar, Deepak B. Chem. Eng. Div., Natl. Chem. Lab. Pune 411 008, India J. Catal., 103(1), 115–25 51-6 (Fossil Fuels, Derivatives, and Related Products)

The silicoaluminophosphate sieves are described in U.S. Pat. Nos. 4,440,871 and 4,654,138, all of the teachings of which are herein incorporated by reference. In addition, European Patent 209,997 discloses the use of silicoaluminophosphates for catalytic dewaxing of lube oils. Other technical articles discussing the structure of these select molecular sieves are as follows:

1) Structure Of An Aluminosilicophosphate, Ito, Masatoki; Shimoyama, Yumiko; Saito, Yoshihikl; Tsurita, Ysaushi; Otake, Masayuki Fac. Sci, Technol., Keio Univ. Yokohama 223, Japan Acta Crystallogr., Sect. C: Cryst. Struct. Commun., C41(12), 1698–700 75-8 (Crystallography and Liquid Crystals)

2) Adsorption Properties Of Microporous Aluminophosphate (A1PO4–5), Stach, H.; Thamm, H.; Fiedler, K.; Grauert, B.; Wieker, W.; Jahn, E.; Oehlmann, G., Cent. Inst. Phys. Chem., Acad. Sci. GDR Berlin-Adlershof 1199, Germ. Dem. Rep. Stud. Surf. Sci. Catal., 28 (New Dev. Zeolite Sci. Technol.), 539–6 66-3 (Surface Chemistry and Colloids)

3) Molecular Sieve Effects In Carboniogenic Reactions Catalyzed By Silioaluminophosphate Molecular Sieves, Pellet, R. J.; Long, G. N.; Rabo, J. A., Union Carbide Corp. Tarrytown, N.Y. 10591, USA, Stud. Surf. Sci. Catal., 28 (New Dev. Zeolite Sci. Technol.), 843–9 45-4 (Industrial Organic Chemicals, Leather, Fats, and Waxes)

4) Methanol Conversion To Light Olefins Over Silicoaluminophosphate Molecular Sieves, Kaiser, Steven W., Union Carbide Corp., South Charleston, W.Va. 25303, USA Arabian J. Sci. Eng., 10(4), 361–6 35-2 (Chemistry of Synthetic High Polymers) 23, 45

5) Synthesis Of Aluminosilicophosphate Molecular Sieves And Their Adsorption-Structural Properties, Pechkovskii, V. V.; Margulets, A. V.; Eschchenko, L. S. BTI USSR Khim. Khim. Tekhnol. (Minsk), 20, 46–50 78-4 (Inorganic Chemicals and reactions)

6) Thermal Stability And Acid Resistance Of Aluminosilicophosphate Zeolites, Margulets, A. V.; Eshchenoko, L. S.; Greben'ko, N. V.; Pechkovskii; V. V. Beloruss. Tekhnol. Inst. Minsk, USSR Izv. Akad. Nauk SSSR, Neorg. Mater., 22(11), 1878–82 66-3 (Surface Chemistry and Colloids)

Suitable borosilicates are exemplified by the following articles:

1) Catalytic And Acidic Properties Of Boron Pentasil Zeolites, Coudurier, G.; Vedrine, J. C. Inst. Rech. Catal., CNRS Villeurbanne F 69626, Fr. Stud. Surf. Sci. Catal., 28 (New Dev. Zeolite Sci. Technol.), 643–52 67-1 (Catalysis, Reaction Kinetics, and Inorganic Reaction Mechanisms)

2) Quantum Mechanical Calculation On Molecular Sieves. 1. Properties Of The Si-O-T (T si, Al, B) Bridge In Zeolites, Derouane, E. G.; Fripiat, J. G., Cent. Res. Lab., Movil Res. and Dev. Corp., Princeton, N.J. 08540, USA, J. Phys. Chem., 91(1), 145–8

3) Acidity And Catalytic Activity For Methanol Transformation Over Modified Borosilicate And Aluminosilicate Zeolites, Hegde, S. G.; Chandwadkar, A. J., Natl. Chem. Lab., Poona 411 008, India, Adv. Catal., [Proc.—Natl. Symp. Catal.], 7th, 163–9. Edited by: Prasada Rao, T.S.R. Wiley: New York 51-11 (Fossil Fuels, Derivatives, and Related Products)

The aluminophosphate, silicoaluminophosphate and borosilicate molecular sieves will have a channel size between $5.5 \times 5.5$ and $4.5 \times 4.5$ Å but excluding $4.5 \times 4.5$ Å as shown in Table 2.

The following Table 2 demonstrates the correct channel size dimensions of the molecular sieve versus other sieves which will not perform with the same adsorption characteristics as a ferrierite-sized molecular sieve.

TABLE 2

| Molecular Sieve | Channel Dimensions (Å) | Size |
|---|---|---|
| chabazite | 3.9 × 4.1 | TOO SMALL |
| zeolite A | 3.9 × 4.1 | TOO SMALL |
| erionite | 3.6 × 5.2 | TOO SMALL |
| Ca-5A | 4.5 × 4.5 | TOO SMALL |
| aluminosilicate ferrierite | 4.5 × 5.5 | CORRECT SIZE |
| aluminophosphate | 4.5 × 5.5 | CORRECT SIZE |
| silicoaluminophosphate | 4.5 × 5.5 | CORRECT SIZE |
| borosilicate | 4.5 × 5.5 | CORRECT SIZE |
| ZSM-5 | 5.4 × 5.6 | TOO LARGE |
| offretite | 6.0 × 6.0 | TOO LARGE |
| mordenite | 6.7 × 7.0 | TOO LARGE |
| omega | 7.4 × 7.4 | TOO LARGE |
| Y zeolite | 7.4 × 7.4 | TOO LARGE |

It is also feasible that the molecular sieve can comprise a large pore zeolite that has been ion exchanged with large cations to diminish the effective channel size of the sieve to within the aforementioned range of dimensions. Thus, any molecular sieve having channel dimensions intermediate those of $5.5 \times 5.5$ and $4.5 \times 4.5$ Å will be considered as candidate of the select molecular sieve of this invention.

Molecular sieves that are too small in pore size do not discriminate between mono-methyl-branched $C_6$ (i.e., methylpentanes) and di-methyl-branched $C_6$ (i.e., dimethylbutanes). In fact, they exclude both and which would therefore result in the passage of only normal paraffins to the isomerization zone. Sieves that are listed as too large do not discriminate properly between normal paraffins and mono-methyl-branched plus di-methyl-branched paraffins. In fact, they adsorb all of these paraffins. Only sieves between, and not including, the pore sizes of the sieves of calcium-5A and ZSM-5 selectively discriminate to accommodate mono-methyl-branched paraffins and normal paraffins while excluding di-methyl-branched $C_6$ paraffins.

As the second configuration for the second product separation zone of the present invention, each absorbent bed contains two sections, each contains a shape-selective molecular sieve having pore sizes of different dimensions. The shape-selective molecular sieve contained in the first section must be one that will effectively adsorb normal paraffins while allowing mono-methyl-branched paraffins and di-branched paraffins to pass to a second molecular sieve. Said molecular sieve will have an apparent pore diameter of 4.5 Å or less. A particularly suitable molecular sieve for the first section is a calcium 5A sieve as described in U.S. Pat. No.

2,883,243 although other divalent exchanged forms of the sieve may also be utilized. With proper choice of the pore sizes the molecular sieve in the first section can be an aluminophosphate, a silicoaluminophosphate or a tectosilicate, like for example, a borosilicate. Other molecular sieves will include the zeolite-R as exemplified in U.S. Pat. No. 3,030,181 or zeolite-T as exemplified in U.S. Pat. No. 2,950,952. It is also foreseeable that the aluminosilicate sieve can be a naturally occurring zeolitic molecular sieve such as chabazite or erionite. The critical dimension of the sieve is the pore diameter existent in the sieve. With a pore diameter of 4.5 Å, but not larger, the normal paraffins will be adsorbed and allow the mono-methyl-branched paraffins and di-branched paraffins to pass through the sieve in the first section to a shape-selective sieve.

The molecular sieve in the second section must be one that will effectively separate mono-methyl-branched paraffins and normal paraffins from more highly branched paraffins (e.g. di-branched paraffins). Suitable molecular sieves in the second section are the same as the particular molecular sieves suitable for the adsorbent beds where a single selective molecular sieve is utilized, as described in the first configuration for the second product separation zone of the present invention. As mentioned above, a molecular sieve having precise pore dimensions intermediate the channel pore dimensions present in either a calcium-5A sieve or a ZSM-5 sieve can be utilized. The particular molecular sieve of this category is capable of adsorbing not only normal hexane but also mono-branched hexanes (methylpentanes) as well. The preferred molecular sieve has eight and ten member rings and pore dimensions between $5.5 \times 5.5$ and $4.5 \times 4.5$ Å, but excluding $4.5 \times 4.5$ Å (i.e., calcium 5A) Angstroms. As a preferred aspect of this form, ferrierite, natural or synthetic, is utilized as the molecular sieve in the second section of the adsorbent bed. This aluminosilicate exhibits a greatly increased adsorption capacity towards methylpentane relative to a calcium-5A molecular sieve. It has been discovered that both the sodium and the hydrogen forms of the ferrierite are viable although it is preferred that the ferrierite be utilized with a cation of an alkali metal, or alkaline earth metal or transition metal cation. Other examples of the suitable molecular sieves of this type include aluminophosphates, silicoaluminophosphates, and borosilicates.

Typically, the bottom stream 9 is fed to the adsorbent beds which operate in a parallel relationship to each other. When any of the adsorbent beds in the second separation zone 10 is saturated with the normal paraffins and mono-branched paraffins, the operation of the bed is changed from an adsorption cycle to a desorption cycle. During this desorption cycle, the valve which controls the flow of the bottom stream 9 into this bed is closed. Normal paraffins and mono-methyl-branched paraffins, e.g. n-pentane, n-hexane, 2-methylpentane, and 3-methylpentane, are desorbed from sieves in the bed and passed, through conduit 14, to the isomerization zone 2 wherein the normal paraffins are isomerized to both mono-methyl paraffins and more highly branched paraffins while the mono-methyl-branched paraffins are isomerized to more highly branched paraffins.

One method that can be utilized to desorb the paraffins from the saturated adsorbent bed involves reducing the pressure in the adsorbent beds. In this method, the pressure in the adsorbent bed is reduced to a pressure which is lower than the pressure used in the adsorption cycle, and the adsorbed paraffins are thereby desorbed from the adsorbent bed.

Another method which can be utilized in the desorption process involves eluting the adsorbed paraffins from the saturated adsorbent bed using a desorbent such as hydrogen or steam.

After the bed is finished with the desorption cycle, the feed valve is opened and the bed is put back to the adsorption cycle. It is not necessary that all of the mono-methyl-branched paraffins and normal paraffins be recycled to the isomerization reactor. However, for economic purposes it is sometimes beneficial that all normal paraffins and mono-methyl branched hexanes be recycled until an equilibrium is reached maximizing the quantity of di-methyl branched hexanes or isopentane.

More highly branched paraffins 11, e.g. 2,3-dimethylbutane, 2,2-dimethylbutanes and any naphthene compounds are not adsorbed in the second separation zone 10, but are permitted to elute through the sieve and are collected, along with the afore-mentioned isopentane 8 recovered from the first product separation zone 6, to form the refinery gasoline pool 13 with the desired high octane rating.

Pre-isomerization Separation

In some instances, the feedstock may contain a high percentage of branched paraffins, e.g. more than 40%, and/or a relatively high concentration of aromatics, e.g. more than 1%. In which instances, the feedstock 1 may be introduced directly to the first product separation zone 6. The high octane rated branched paraffins, i.e. isopentane, 2,3 dimethyl butane, 2,2 dimethyl butane, and aromatics and naphthenes, if present, are separated and recovered as product gasoline in the first product separation zone 6 and the second product separation zone 10. The remaining normal paraffins, 2-methyl pentane and 3-methyl pentane, which have low octane ratings, are thereafter sent from the second product separation zone to the isomerization zone 2 and are isomerized to produce branched paraffins.

One advantageous aspect of this pre-isomerization separation is the fact that the high octane rated branched paraffins, i.e. isopentane, 2,3 dimethyl butane and 2,2 dimethyl butane are not passed to the isomerization zone 2. The isomerization reaction has a chemical equilibrium. The exclusion of the pre-existing dimethyl paraffins and isopentane from the isomerization zone is advantageous for maximizing the quantity of di-methyl paraffins and isopentane produced during isomerization while at the same time, reducing the number of normal paraffins which remain unisomerized in the isomerization zone effluent stream. Isopentane is recovered from the first product separation zone 6 as the top product stream 8 to form part of the refinery gasoline pool 13. Di-branched paraffins, including 2,3 dimethyl butane and 2,2 dimethyl butane, are not adsorbed in the second separation zone 10 and are collected as part of the product stream 11 to form part of the refinery gasoline pool 13.

Another advantageous aspect of the pre-isomerization separation is the fact that the aromatics are not passed to the isomerization zone 2. Aromatics, when present, tend to generate a large quantity of heat in the isomerization zone 2 as a result of hydrogenation. Therefore, where the feedstock contains a relative high concentration of aromatics, e.g. more than 1% by weight, the pre-isomerization separation of the aromatics is particularly desired to avoid the possibility of the overheating of the reactor. Moreover, some of the aromatics have relatively high octane ratings and would make useful additions to the gasoline pool. These aromatics will not be adsorbed by the separation sieves in the second product separation zone and will pass with the high octane dimethyl paraffins and can, therefore, be conveniently recovered as part of the stream 11 to form part of the product gasoline pool 13. Naphthenes, some of which also have relatively high octane rating, when present, will also be advantageously separated and recovered along with the aromatics as product stream to form part of the refinery gasoline pool 13.

The ranges and limitations provided in the instant specification and claims are those which are believed to particularly point out and distinctly claim the instant invention. It is, however, understood that other ranges and limitations that perform substantially the same function in substantially the same manner to obtain the same or substantially the same result are intended to be within the scope of the instant invention as defined by the instant specification and claims.

What is claimed is:

1. An integrated process for producing a gasoline blending component with increased octane value from a hydrocarbon feed stream comprising $C_5$ paraffins and $C_6$ paraffins, said process comprising:
   (a) passing said hydrocarbon feed stream to an isomerization zone maintained at isomerizaton conditions and containing an isomerization catalyst whereby said hydrocarbon feed stream is isomerized to produce an isomerization zone effluent stream comprising di-branched paraffins, mono-methyl-branched paraffins and unreacted normal paraffins;
   (b) passing said isomerization zone effluent stream to a first product separation zone;
   (c) separating said isomerization zone effluent stream into at least two streams:
      1) a first product separation zone product stream comprising mono-methyl-branched-pentane, and
      2) a first product separation zone bottom stream comprising $C_5$ normal paraffins, $C_6$ normal paraffins, $C_6$ mono-branched paraffins and $C_6$ di-branched paraffins;
   (d) recovering said first product separation zone product stream comprising mono-methyl-branched pentane from step (c), as part of said gasoline blending component;
   (e) passing said first product separation zone bottom stream from step (c) to a second product separation zone and separating said first product separation zone bottom stream into at least two stream:
      1) a second product separation zone effluent stream comprising di-branched paraffins;
      2) a second product separation zone recycle stream comprising mono-methyl-branched paraffins and normal paraffins;
   (f) recovering said second product separation zone recycle stream comprising mono-methyl-branched paraffins and normal paraffins from (e), and recycling at least a portion thereof to said isomerization zone; and
   (g) recovering said second product zone effluent stream from (e) as part of said gasoline blending component.

2. The process of claim 1, wherein said first product separation zone product stream from step (c) and said second product zone effluent stream from step (d) are combined to provide a product suitable for use in a refinery gasoline pool.

3. The process of claim 1, wherein said first product separation zone comprises a fractional distillation device.

4. The process of claim 1, wherein said second product separation zone comprises a ferrierite aluminosilicate having pore sizes between $5.5 \times 5.5$ and $4.5 \times 4.5$ Å and excluding $4.5 \times 4.5$ Å.

5. The process of claim 1, wherein said second product separation zone comprises multiple sections, each contains crystalline molecular sieves having pore sizes of different dimensions:
   wherein at least one of the sections contain a first type molecular sieve having pores of a dimension effective to adsorb normal paraffins while being restrictive to prohibit adsorption of mono-methyl-branched paraffins and di-branched paraffins; and
   wherein at least one of the sections contains a second type molecular sieve having a pore size between $5.5 \times 5.5$ and $4.5 \times 4.5$ Å and is effective to adsorb normal paraffins and mono-methyl-branched paraffins while restrictive to prohibit adsorption of di-branched paraffins.

6. The process of claim 5, wherein said first type molecular sieve comprises calcium 5A aluminosilicate having pores of smaller dimension than said second sieve.

7. The process of claim 5, wherein said second type molecular sieve comprises a ferrierite aluminosilicate having pore size between $5.5 \times 5.5$ and $4.5 \times 4.5$ Å.

8. The process of claim 5, wherein said second type molecular sieve of said second product separation zone comprises ferrierite.

9. The process of claim 5, wherein said second type molecular sieve of said second product separation zone is selected from the group consisting of tectosilicates, aluminophosphates and silicoaluminophosphates.

10. The process of claim 5, wherein said second type molecular sieve comprises a tectosilicate having pore sizes between $5.5 \times 5.5$ and $4.5 \times 4.5$ Å, which tectosilicate has cations exchanged therewith selected from the group consisting of an alkali metal, an alkaline earth metal and transition metal cations.

11. The process of claim 10, wherein said tectosilicates are selected from the group consisting of aluminosilicates and borosilicates.

12. The process of claim 1, wherein said more highly branched paraffins comprise 2,2-dimethylbutane and 2,3-dimethylbutane.

13. The process of claim 1, wherein said isomerization catalyst comprises an aluminosilicate having a Group VIII metal dispersed thereon.

14. The process of claim 13, wherein said aluminosilicate is mordenite and said Group VIII metal is platinum.

15. An integrated process for producing a gasoline blending component with increased octane value from a hydrocarbon feed stream comprising $C_5$ paraffins and $C_6$ paraffins, said process comprising:
   (a) passing said hydrocarbon feed stream to a first product separation zone and separating said feed stream into at least two streams:
      1) a first product separation zone product stream comprising mono-methyl-branched-pentane, and
      2) a first product separation zone bottom stream comprising $C_5$ normal paraffin, $C_6$ normal paraffin, $C_6$ mono-branched paraffins and $C_6$ di-branched paraffins;

(b) recovering from said first product separation zone product stream comprising said mono-methyl-branched-pentane from step (a), as part of said gasoline blending component;

(c) passing said first product separation zone bottom stream from step (a) to a second product separation zone and separating said first product separation zone bottom stream into at least two streams:
1) a second product separation zone effluent stream comprising di-branched paraffins,
2) a second product separation zone recycle stream comprising mono-methyl-branched paraffins and normal paraffins;

(d) recovering said second product zone effluent stream in (c) as part of said gasoline blending component;

(e) recovering said second product separation zone recycle stream from (c);

(f) passing at least a portion of the recovered second product separation zone recycle stream comprising mono-methyl-branched paraffins and normal paraffins from (e) to an isomerization zone maintained at isomerization conditions and containing an isomerization catalyst whereby said hydrocarbon feed stream is isomerized to produce an isomerization zone effluent stream comprising di-branched paraffins, mono-methyl-branched paraffins and unreacted normal paraffins;

(g) passing said isomerization zone effluent stream in (f) to said first product separation zone in (a).

16. The process of claim 15, wherein said hydrocarbon feed stream further comprises more than 1% by weight of aromatics, and the aromatics are recovered along with said more highly branched paraffins as part of the second product zone product effluent stream which forms part of said gasoline blending component.

17. The process of claim 16, wherein said second product separation zone comprises a ferrierite aluminosilicate having pore sizes between $5.5 \times 5.5$ and $4.5 \times 4.5$ Å and excluding $4.5 \times 4.5$ Å.

18. The process of claim 15, wherein more than 40% of the paraffins in said hydrocarbon feed stream are branched paraffins.

19. The process of claim 18, wherein said second product separation zone comprises a ferrierite aluminosilicate having pore sizes between $5.5 \times 5.5$ and $4.5 \times 4.5$ Å and excluding $4.5 \times 4.5$ Å.

20. An integrated process to produce a gasoline blending component with increased octane value from a hydrocarbon feed stream comprising $C_5$ paraffins and $C_6$ paraffins, said process comprising:

(a) passing said hydrocarbon feed stream to an isomerization zone maintained at a temperature of 200° C. to 400° C. and a pressure of from about 10 bar to about 40 bar and containing an isomerization catalyst comprising platinum dispersed on mordenite in a weight concentration of from about 0.2 to about 0.4 wt % whereby said hydrocarbon feed stream is isomerized to produce an isomerization zone effluent stream comprising di-branched paraffins, mono-methyl-branched paraffins and unreacted n-pentane and n-hexane;

(b) passing said isomerization zone effluent stream to a first product separation zone comprising a fractional distillation device;

(c) separating said isomerization zone effluent stream into at least two streams:
1) a first product separation zone product stream comprising mono-methyl-branched-pentane (isopentane),
2) a first product separation zone bottom stream comprising $C_5$ normal paraffins, $C_6$ normal paraffins, $C_6$ mono-branched paraffins and $C_6$ di-branched paraffins;

(d) recovering said first product separation zone product stream comprising mono-methyl-branched-pentane from step (c);

(e) passing said first product separation zone bottom stream from step (c) to a second product separation zone comprising crystalline molecular sieves whereby normal paraffins and mono-branched paraffins are adsorbed, and di-branched paraffins are permitted to pass through, wherein said second product separation zone comprises two sections, wherein the sieves of a first section of said second product separation zone comprises calcium 5A aluminosilicate, and wherein the sieve of a second section of said second product separation zone comprises a sieve selected from the group comprising (1) ferrierite aluminosilicate having pore size between $5.5 \times 5.5$ and $4.5 \times 4.5$ Å, and (2) a tectosilicate having pore sizes between $5.5 \times 5.5$ and $4.5 \times 4.5$ Å, which tectosiliate has cations exchanged therewith selected from the group consisting of an alkali metal, an alkaline earth metal and transition metal cations;

(f) recovering from said second product separation zone a second product separation zone effluent stream comprising 2,3-dimethylbutane and 2,2-dimethylbutane as second product separation zone effluent stream;

(g) desorbing the normal paraffins and mono-branched paraffins adsorbed in said second product separation zone with hydrogen to form a second product separation recycle stream;

(h) recycling at least a part of said second product separation zone recycle stream from (g) to the isomerization reactor; and (i) collecting as gasoline blending component said second product separation zone effluent stream comprising 2-methylpentane and 3-methylpentane from (f), and said first product separation zone product stream comprising mono-methyl-branched-pentane from (d).

* * * * *